United States Patent [19]

Patureau et al.

[11] 4,249,655
[45] Feb. 10, 1981

[54] CYCLONE DUST ANALYZER FOR DETERMINING MICRODUST CONTENT IN FIBERS

[75] Inventors: Myles A. Patureau, New Orleans, La.; Michael F. Murray, Newville, Ala.

[73] Assignee: The United States of America as represented by the Secretary of Agriculture, Washington, D.C.

[21] Appl. No.: 53,476

[22] Filed: Jun. 29, 1979

[51] Int. Cl.³ .......................... B07B 7/06; B07B 9/02
[52] U.S. Cl. ........................................ 209/31; 209/3;
209/237; 209/250; 209/144; 73/432 PS; 73/28;
73/159; 55/270
[58] Field of Search ............... 209/1, 3, 10, 17, 21–23,
209/30, 31, 144, 237, 250; 93/28, 432 PS, 159;
162/49; 55/270

[56] References Cited

U.S. PATENT DOCUMENTS

| | | | |
|---|---|---|---|
| 2,651,812 | 9/1953 | Black | 209/144 |
| 3,543,931 | 12/1970 | Rastatter | 209/211 |
| 3,620,370 | 11/1971 | Swayze | 209/144 |
| 3,756,400 | 9/1973 | Kammori et al. | 209/1 |
| 3,918,585 | 11/1975 | Hagelstam | 209/3 |
| 4,046,593 | 9/1977 | Au et al. | 55/270 X |
| 4,154,111 | 5/1979 | Anderson et al. | 73/432 PS |
| 4,155,247 | 5/1979 | Kaczmarek et al. | 73/28 |

*Primary Examiner*—Ralph J. Hill
*Attorney, Agent, or Firm*—M. Howard Silverstein; Raymond C. Von Bodungen; David G. McConnell

[57] ABSTRACT

An apparatus for removing dust from a fiber sample for subsequent analysis is disclosed. A first upper cylindrical chamber containing a fiber sample has a tangential air jet and a radial air jet installed to swirl and tumble the fiber sample in a cyclonic fashion, thus liberating the dust from the sample when either a positive or a negative pressure is applied through the air jets. The liberated dust particles are then screened out through a 100 mesh screen filter and exhausted through a funnel. The device can be equipped with a second stage chamber containing a plurality of step-stage filters and a third stage plurality of microfilters to selectively screen the dust particles. A blow bottle containing an aqueous medium to absorb even the finest dust particles or gas can also be added as a fourth stage.

13 Claims, 3 Drawing Figures

DETAIL A ized and weighed according to ASTM Standards. (American Society for Testing and Materials, Committee D-13, ASTM Designation, D-1776, ASTM Standards, Part 32, Philadelphia, 1977). The sample is placed in a first upper cylindrical chamber 1 of the device and the top 5 is secured. The instant device was designed with a top to pressure fit. However, any means of inserting a sample would be satisfactory. For example, the cylinder could be made into two halves which would screw together. Either positive or negative pressure can be applied. In the case of the instant invention, negative pressure was used. A vacuum is applied to the lower end of the microfilter 9, through negative pressure tube 11. The vacuum creates a suction through the microfilter 9 step-stage screens 7, and through the small jets 2 and 3 of upper cylindrical chamber 1. This causes a high velocity jet of air to be taken in at tangential jet 2, which causes the cotton containing the dust particles to be swirled in a cyclonic motion around the inside wall of the upper cylindrical chamber 1. The cyclonic motion liberates the fibers of dust, which pass through a 100 mesh screen 4 trapping fiber dust of 100 microns or greater and then into step-stage filter screen 7 and then through microfilter 10. Dust is selectively screened out in each stage by the size of the screens installed. At the same time, the radial jet creates a high velocity stream of air over 100 mesh screen 4 to tumble the fiber sample in a rolling motion. This action prevents fibers and trash from collecting on filter screen 4. The vacuum force which causes the cyclonic action in upper cylindrical chamber 1, also simultaneously pulls the liberated microparticles onto the microfilter 10.

CYCLONE DUST ANALYZER FOR DETERMINING MICRODUST CONTENT IN FIBERS

BACKGROUND OF THE INVENTION

1. Field of the Invention

The instant invention relates to an apparatus for extracting microdust from fiber samples for use in laboratory analysis.

2. Description of the Prior Art

A means of analyzing the microdust in cotton which causes lung disorders and diseases has become an important field of research in the textile industry. Other associated industries with respirable particle health problems are also interested in tools and techniques for enabling them to analyze and study dust particles in the microscopic range. Therefore, an instrument and method for quickly liberating microparticles from fibers, grain, etc., is of prime importance in these studies.

Numerous methods such as the Shirley Analyzer and SRRL Non-Lint Tester are being used currently in the field for cleaning and separating trash and large particles from cotton. However, the microdust portion of the non-lint content cannot be measured by these instruments. Other methods used for removing microdust from fibers include the Sonic Vibrator which shakes the dust from cotton samples through filter screens. This method is long and time consuming. Another apparatus and method currently used in the cotton industry is to rigidly support a mat of fiber to be sampled and blow air through the mat with high pressure spray jets. The dust is then collected on a filter in back of the fibers. With this method, the fibers are not agitated and microdust particles remain in the cotton undetected.

SUMMARY OF THE INVENTION

The instant invention is an analytical device developed to remove fiber dust particles from a preweighed, preconditioned fiber sample. The device liberates dust from the sample selectively screening the dust into as many sizes as preprogrammed. This dust can then be studied and analyzed.

A first upper cylindrical chamber containing a fiber sample is equipped with an upper tangential air jet and a lower radial air jet to swirl and tumble a fiber sample in a cyclonic fashion and thus to liberate fiber dust particles when either a positive or negative pressure is applied. The dust is filtered on a screen located at the base or lower exhaust end of the first upper cylindrical chamber. A funnel arrangement is provided to gather the exhaust from the first upper cylindrical chamber after passing through the filter screen and the exhaust is either directed into the atmosphere or to subsequent processing. The funnel is also provided as a means of hooking up a vacuum to the device if negative pressure is desired.

DESCRIPTION OF THE PREFERRED EMBODIMENTS

In general, the operation of the apparatus is as follows: A sample of cotton fibers containing foreign matter and dust particles is atmospherically condition- If only 100 micron particles or larger are desired to be screened out, the microfilter is not attached and the vacuum is drawn from the lower exit (exhaust) end cylinder 1.

Figure 2:
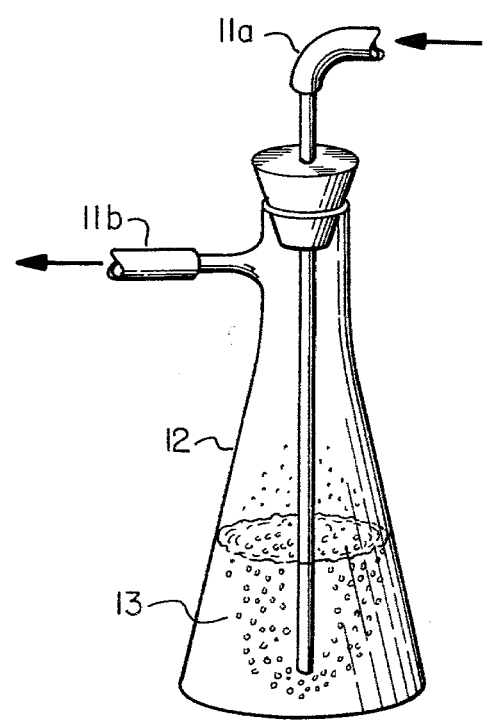
FIG. 2 is a side elevational view having an optional apparatus attachment with aqueous medium for trapping gasses or small particles which may escape the micropore filter.

Therefore, a separation of particles by size is accomplished by a step-stage series of filters before collecting the microdust particles on micropore or millipore filters located in steps and stages of filtering chamber 6. Additional collection of very fine particles of dust and gasses can be accomplished by adding an additional filtering stage consisting of a reverse blow bottle, as shown in FIG. 2. This bottle would contain any liquid aqueous medium designed to trap even the smallest invisible particle of dust or possibly a gas contaminant. The vacuum would then draw the exhaust from filtering chamber 9 through a tube 11a and through the reverse blow bottle and then vacuum containing tube 11b. The aqueous medium 13 would then absorb the dust particles or gas desired to be collected, and subsequent analysis would be performed using a particle counter, electron microscope, or gas chromatograph.

Figure 1:
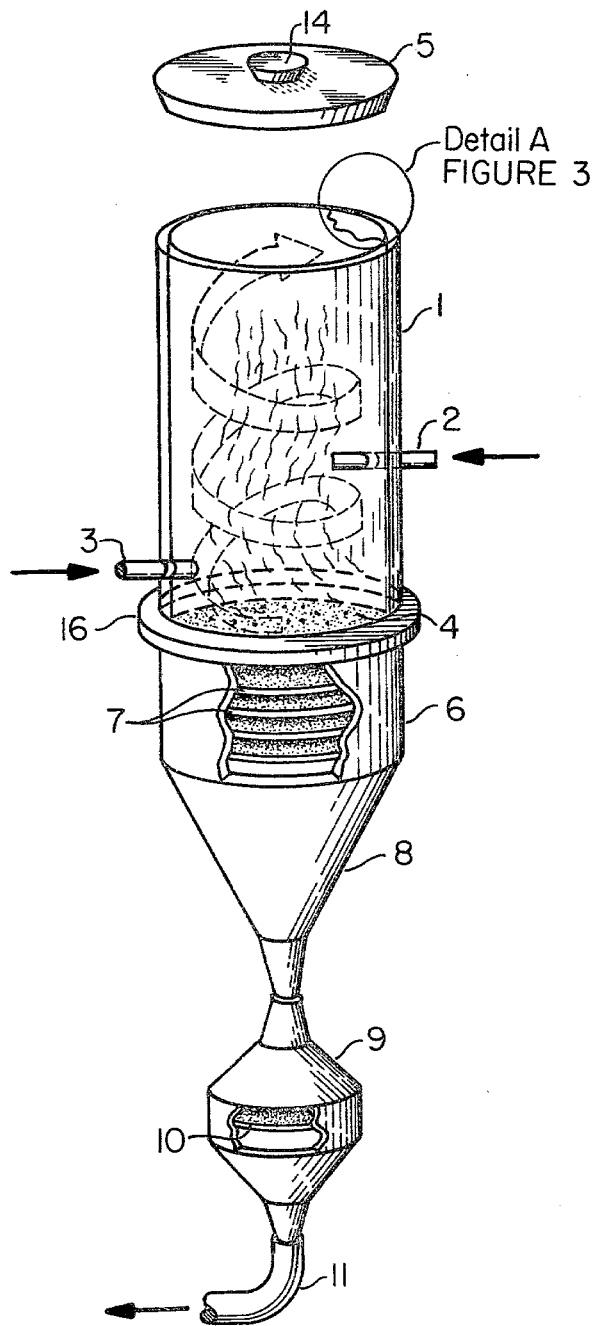
FIG. 1 is an exploded cut away side elevational view of the microdust collector.
Figure 3:
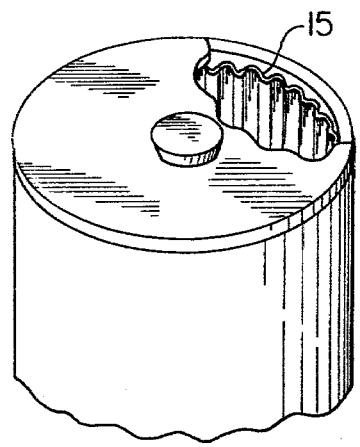
FIG. 3, Detail A, shows another embodiment of the instant invention wherein the upper cylindrical chamber's inner surface is corrugated for more efficient cleaning.

More specifically, FIG. 1 shows a first upper and cylindrical chamber 1 which is a pre-formed plexiglass cylinder. The diameter, thickness, and length may vary, however, the instant apparatus is 2 inches in diameter, ¼ inches thick and 3½ inches high. The inside of cylinder 1 may be smooth or provided with a corrugated surface 15 (see FIG. 3) as to improve the cleaning efficiency.

The cylinder may be any material; plastic, metal, etc. Clear plexiglass was used to enable one to view the device in operation. Upper cylindrical chamber 1 is open on the top and bottom. Into and through the walls of cylinder 1 are affixed two small tubular jets 2 and 3. The size of the jets may vary, however, the instant invention uses ⅛ inch diameter jets. Jet 2 is an upper tangential jet, and is located approximately mid-way of first or upper chamber 1's height. Jet 2 is through the cylinder wall and is tangential to the periphery or inner surface of cylinder 1.

Lower jet 3 is a radial jet, and is located ⅛ inches above a first stage filter screen 4. It also is affixed through the wall of cylinder 1 but is parallel to the radius of cylinder 1. First stage filter screen 4 (a 100 micro screen filter) is affixed to the bottom of cylinder 1 by snap ring assembly 16. The size of the filter mesh of first stage filter 4 may vary, however, the instant apparatus uses a screen of 100 mesh per linar inch. The filter is simply put in place and removed by means of the snap ring arrangement 16.

A cover 5 is provided for the opening in the top of cylindrical plexiglass chamber 1. The cover may be screwed, clamped, or fastened in any satisfactory means. However, the instant apparatus uses a snug pressure fit cover because a vacuum is used in the operation. There is a handle or knob 14 located approximately in the center of cover 5. This knob 14 is provided to allow the operator to remove the top or cover 5 easily.

A lower or second chamber 6 is constructed so as to receive the base of upper cylindrical chamber 1 with a snug pressurefit. However, a screw, clamp or any satisfactory method of attachment can be used. Lower chamber 6 contains a plurality step-stage filter screens 7 which are appropriately spaced apart. The screens may vary in size and distribution depending on the size particles desired to be collected and thus as many steps or sizes of screen are added to sufficiently screen out and select dust particles for analysis as desired.

When only a first upper cylinder chamber is used, then a funnel or cone 8 whose large circumference opening is complimentary to and affixed to the outside circumference of the base of the first upper cylindrical chamber forming a pressure fit when fitting between the base of said cylindrical chamber 1 and said funnel 8. Therefore, funnel 8 is juxtaposed below filter screen 4 so as to receive exhaust from first upper cylindrical chamber 1. When a second chamber 6 is affixed for additional selectivity of dust particles, then funnel 8 is attached to the exhaust end of chamber 6 and, chamber 6 is affixed to the exhaust ends of first upper cylindrical chamber 1. Microfilter holder 9 forms a third chamber and is attached to the exhaust of second chamber 6. Again, funnel or cone 8 may be screwed on, clamped or fastened in any satisfactory means to the lower exhaust end of either first cylindrical chamber 1 or second chamber 6. However, the instant invention uses a snug pressure fit since it operates under vacuum pressure and the vacuum holds first chamber 1, second chamber 6, and funnel 8 tightly together.

A micro filter holder furnishing a third chamber is affixed to the exhaust end of funnel 8. This microfilter holder can again screen out even smaller particles of dust for detailed analysis. The microfilter holder contains a plurality of microfilters 10 which are 8-10 microns in size. These microfilters are manufactured by Millipore Corporation, Bedford, Massachussetts.

A vacuum of 12 inches of mercury is applied to the lower end of microfilter holder 11. The amount of vacuum, however, can vary with the degree of sample agitation desired. There is a slight flow drop proportional to the amount of dust that is accumulated on the microfilter. This flow drop, however, does not interfere with the action of the cyclone dust analyzer.

Thus, as vacuum is applied to the lower end of third chamber microfilter holder 11, it causes a flow of air through the device. Air enters through jets 2 and 3. Air entering through jet 2 causes the cotton sample containing the dust particles to swirl in a cyclonic motion around the inside of the chamber. Air entering through jet 3, which is a radial jet, tumbles the fiber in a rolling motion. This combination of actions on the cotton sample by jets 2 and 3 liberates the dust particles and causes them to begin to screen out on the preselected filter sizes. The larger particles are caught on the 100 mesh screen at the bottom of first chamber 1. Dust particles passing through 100 mesh screen 4 pass into second chamber 6 which is a step-stage filter and are screened out by preselected filters 7 which are different sizes and are located in second chamber 6. As many sizes and steps can be added as desired for preselection of sizes. The dust particles are then passed through third stage 9 and particles filtered out by microfilter 10.

Of course, if even finer particles of dust or entrapped gases are desired to be collected and analyzed, then a fourth filtering stage as shown in FIG. 2 is added and the vacuum is attached downstream of fourth filtering stage 12. This stage would be a reverse blow bottle 12 containing a liquid or aqueous medium 13 preselected and designed to capture either gas or dust particles.

Particles smaller than the pores of the microfilter (8-10 microns) may also be collected by using blow bottle 12, FIG. 2 in a series with third chamber 9 and drawing the vacuum from the air end of 11b bottle 12. Bottle 12 is appropriately connected to third chamber 9 at end 11 and to the vacuum source using rubber tubing. Blow bottle 12 is filled with an aqueous medium as desired for collection. If one desires to capture and analyze a chemical or gas which may exist in the sample then the aqueous medium can be changed to absorb the gas or chemical desired to be trapped and subsequently analyzed. Needless to say the aqueous liquid would be campatible with trapping the desired gas or chemical to be analyzed.

If positive pressure is desired to be used instead of vacuum, then it should be understood that all the connections made between first chamber 1, second chamber 6, funnel 8, and third chamber 9 will have to be screw or clamp type or some means necessary to contain positive pressure within the device rather than pressure contact fittings as used in the instant explanation for vacuum pressure.

We claim:

1. An apparatus for removing filter dust particles from fiber for sampling and analysis comprising:
    (a) a first upper cylindrical chamber having an opening on the bottom end thereof and containing a preconditioned and preweighed fiber sample, said sample containing fiber dust particles to be removed and analyzed;
    (b) an upper, tangential air jet, located into and through the wall of the first upper cylindrical chamber and periphery tangential to the periphery or inner surface of said first chamber, thus, enabling air to be directed in a tangential manner into the fiber sample contained therein, thereby causing the fiber sample to swirl inside the first chamber in a cyclonic motion when a negative pressure is applied to first chamber and thus liberate fiber dust particles from the fiber sample;

(c) a radial air jet affixed into and through the wall of the first upper cylindrical chamber, said radial air jet being located parallel to the radius of the first cylindrical chamber so as to direct air in a radial manner to tumble the fiber sample in a rolling motion and blow air over a filter screen;

(d) said filter screen affixed to the opened bottom end of said first upper cylindrical chamber to entrap the liberated fiber dust particles for subsequent analysis.

(e) a funnel whose large circumference opening is complimentary to and affixed to the outside circumference of the opened bottom of the first upper cylindrical chamber thus forming a pressure fitting between the base of said cylindrical chamber and said funnel juxtaposed below the filter screen so as to receive the exhaust from the upper cylindrical chamber through said filter screen.

2. The apparatus as defined in claim 1 including a second chamber, said chamber constructed to receive the base of the first upper cylindrical chamber and thereby form an air-tight snug pressure fit between the two chambers, and said funnel affixed to the lower or exhaust end of said second chamber.

3. The apparatus as defined in claim 1 including an opening in the top of said first upper cylindrical chamber and a cover provided for said opening thereby allowing a fiber sample to be introduced into said first upper cylindrical chamber.

4. The apparatus as defined in claim 1 wherein the tangential jet is located approximately mid-way of the first or upper cylindrical chamber's height.

5. The apparatus of claim 1 wherein the radial jet is located approximately $\frac{1}{8}$th inches above the filter screen.

6. The apparatus as defined in claim 1 wherein the filter screen is a 100 mesh screen and is affixed to the opened end bottom of the cylindrical chamber by means of a snap ring.

7. The apparatus as defined in claim 1 wherein the inside wall surface of the upper cylindrical chamber is corrugated to improve cleaning efficiency.

8. The apparatus as defined in claim 1 wherein the upper cylindrical chamber is constructed of clear plexiglass.

9. The apparatus as defined in claim 2 wherein the second chamber includes a plurality of step-stage filters appropriately spaced apart.

10. The apparatus as defined in claim 9 including a microfilter holder attached to the lower or exhaust end of the funnel.

11. The apparatus as defined in claim 10 wherein the microfilter holder includes a plurality of spaced apart microfilters.

12. The apparatus as defined in claim 11 including a blow bottle attached to the exhaust end of the microfilter holder, said blow bottle containing an aqueous medium to absorb fiber dust particles to be subsequently analyzed.

13. The apparatus as defined in claim 12 wherein the aqueous medium is used to absorb gasses to be subsequently analyzed.

* * * * *